US009784675B2

(12) United States Patent
Cooke (10) Patent No.: US 9,784,675 B2
(45) Date of Patent: Oct. 10, 2017

(54) OPTICAL TARGET ORIENTING SYSTEM AND METHOD

(71) Applicant: The Boeing Company, Chicago, IL (US)

(72) Inventor: Barry T. Cooke, Black Diamond, WA (US)

(73) Assignee: The Boeing Company, Chicago, IL (US)

( * ) Notice: Subject to any disclaimer, the term of this patent is extended or adjusted under 35 U.S.C. 154(b) by 92 days.

(21) Appl. No.: 14/918,790

(22) Filed: Oct. 21, 2015

(65) Prior Publication Data

US 2017/0115111 A1    Apr. 27, 2017

(51) Int. Cl.

| | |
|---|---|
| *G01B 11/14* | (2006.01) |
| *G01N 21/47* | (2006.01) |
| *G01C 15/02* | (2006.01) |
| *G01S 7/481* | (2006.01) |
| *G01S 17/66* | (2006.01) |

(52) U.S. Cl.
CPC ......... *G01N 21/4785* (2013.01); *G01C 15/02* (2013.01); *G01S 7/481* (2013.01); *G01S 17/66* (2013.01)

(58) Field of Classification Search
CPC .......... G01S 13/00; G01S 15/00; G01S 17/00; G01S 13/422; G01S 17/66; G01S 17/42; G01S 17/08; G01S 13/08; G01S 13/42; G01S 15/08; G01B 11/00; G01B 11/14; G01B 11/026; G01N 21/4785; A63F 9/0613; F16M 11/043
See application file for complete search history.

(56) References Cited

U.S. PATENT DOCUMENTS

| | | | | |
|---|---|---|---|---|
| 2,740,962 | A * | 4/1956 | Hammond, Jr. | ...... G01S 13/422 318/691 |
| 4,799,687 | A * | 1/1989 | Davis | ..................... A63F 9/0613 273/358 |
| 6,420,694 | B1 | 7/2002 | Greenwood | |
| 8,237,934 | B1 * | 8/2012 | Cooke | ..................... G01S 17/66 356/614 |
| 2015/0192241 | A1 * | 7/2015 | Shannahan | .......... F16M 11/043 248/178.1 |

OTHER PUBLICATIONS

Active Target™, Motorized Laser Tracking Target, Automated Precision, Inc. (not dated).
Loser, Raimund (Hexagon Metrology),"Active Reflector," 31st Annual Coordinate Metrology Society Conference (Jul. 22, 2015).

* cited by examiner

*Primary Examiner* — Jamil Ahmed
(74) *Attorney, Agent, or Firm* — Walters & Wasylyna LLC (57) ABSTRACT

An optical target orienting system including a mount defining a pan axis, an optical target positioned on the mount, the optical target being rotatable relative to the mount about a tilt axis, a pan assembly operatively connected to the mount to rotate the mount and, thus, the optical target about the pan axis, and a tilt assembly operatively connected to the optical target to rotate the optical target relative to the mount about the tilt axis.

21 Claims, 6 Drawing Sheets

OPTICAL TARGET ORIENTING SYSTEM AND METHOD

FIELD

This application relates to optical metrology and, more particularly, to optical targets useful for optical dimensional metrology.

BACKGROUND

The aircraft manufacturing process involves precision fabrication and assembly of large components, such as fuselage shell structures and wings. The position and orientation of components during fabrication and assembly require demanding tolerances. To satisfy demanding tolerances, information about a given component, such as information about the dimensions (e.g., surface contour) of the component or information about the location/orientation of the component, must be very accurate.

Thus, optical dimensional metrology techniques are commonly employed during the aircraft manufacturing process. For example, laser trackers are commonly used to perform various positioning and measuring functions during aircraft assembly. By projecting a laser beam at an optical target mounted to the object being measured, a laser tracker (or other apparatus employing a laser for dimensional metrology) can perform measurements at very high resolution, and can provide very accurate geometric dimensional data.

Retroreflectors are commonly used as optical targets because they reflect light back toward the source of the light (e.g., the laser tracker). Various retroreflectors are presently available with relatively large acceptance angles. However, when a light source is outside of the acceptance angle, such as when multiple spaced apart laser trackers are measuring the same optical target, the retroreflector must be moved into better alignment with the light source. The process of orienting retroreflectors into alignment with light sources can be time consuming and, therefore, expensive, particularly when the object being measured is relatively large.

Accordingly, those skilled in the art continue with research and development efforts in the field of optical dimensional metrology.

SUMMARY

In one embodiment, the disclosed optical target orienting system may include a mount defining a pan axis, an optical target positioned on the mount, the optical target being rotatable relative to the mount about a tilt axis, a pan assembly operatively connected to the mount to rotate the mount and, thus, the optical target about the pan axis, and a tilt assembly operatively connected to the optical target to rotate the optical target relative to the mount about the tilt axis.

In another embodiment, the disclosed optical target orienting system may include a mount defining a pan axis, a spherically mounted retroreflector positioned on the mount, the spherically mounted retroreflector being rotatable relative to the mount about a tilt axis, a pan assembly operatively connected to the mount to rotate the mount and, thus, the spherically mounted retroreflector about the pan axis, and a tilt assembly operatively connected to the spherically mounted retroreflector to rotate the spherically mounted retroreflector relative to the mount about the tilt axis.

In yet another embodiment, the disclosed optical target orienting system may include a mount defining a nest and an underside surface opposed from the nest, the mount including a shaft extending from the underside surface along a pan axis, a spherically mounted retroreflector positioned in the nest, the spherically mounted retroreflector being rotatable relative to the mount about a tilt axis, wherein the tilt axis is perpendicular to the pan axis, a first servo motor operatively connected to the shaft to rotate the mount about the pan axis, and a second servo motor operatively connected to the spherically mounted retroreflector to rotate the spherically mounted retroreflector relative to the mount about the tilt axis.

In one embodiment, the disclosed optical target orienting method may facilitate orienting a spherically mounted retroreflector that is positioned on a mount. The method may include the steps of (1) operatively connecting a pan actuator to the mount such that actuation of the pan actuator causes the mount to rotate about a pan axis, (2) operatively connecting a tilt actuator to the spherically mounted retroreflector such that actuation of the tilt actuator causes the spherically mounted retroreflector to rotate relative to the mount about a tilt axis, and (3) actuating at least one of the pan actuator and the tilt actuator.

Other embodiments of the disclosed optical target orienting system and method will become apparent from the following detailed description, the accompanying drawings and the appended claims.

DETAILED DESCRIPTION

The disclosed optical target orienting system may facilitate remotely orienting a retroreflector into alignment with a light source, thereby eliminating the need for manually manipulating the retroreflector to achieve the desired alignment. Significantly, the disclosed optical target orienting system may employ a certified retroreflector and a certified mount in a manner that does not affect the certification of the retroreflector or the certification of the mount. Therefore, when a certified retroreflector and a certified mount are used, the disclosed optical target orienting system need not be separately certified, thereby significantly reducing complexity and cost.

Figure 1:
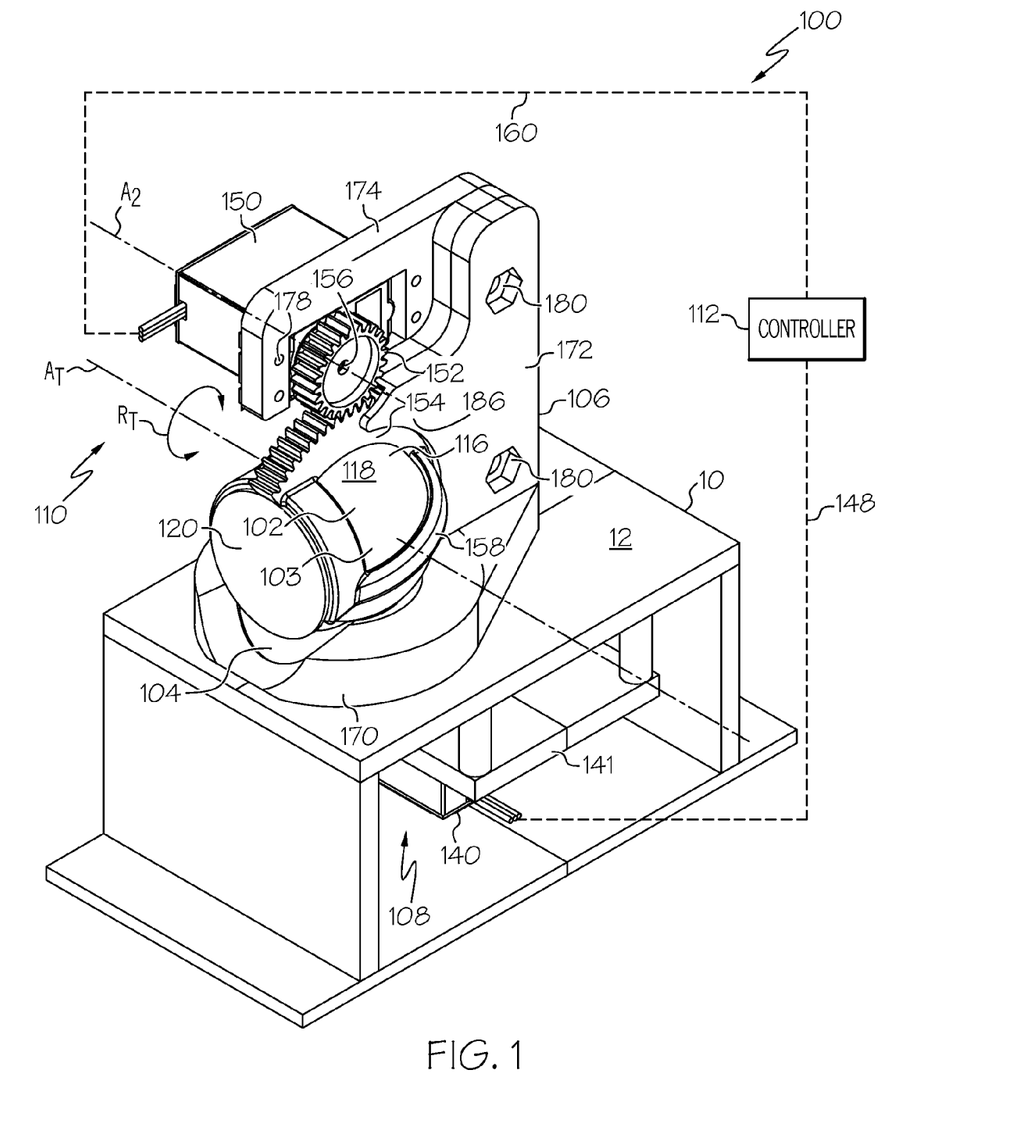
FIG. 1 is a front and side perspective view of one embodiment of the disclosed optical target orienting system.
Figure 2:
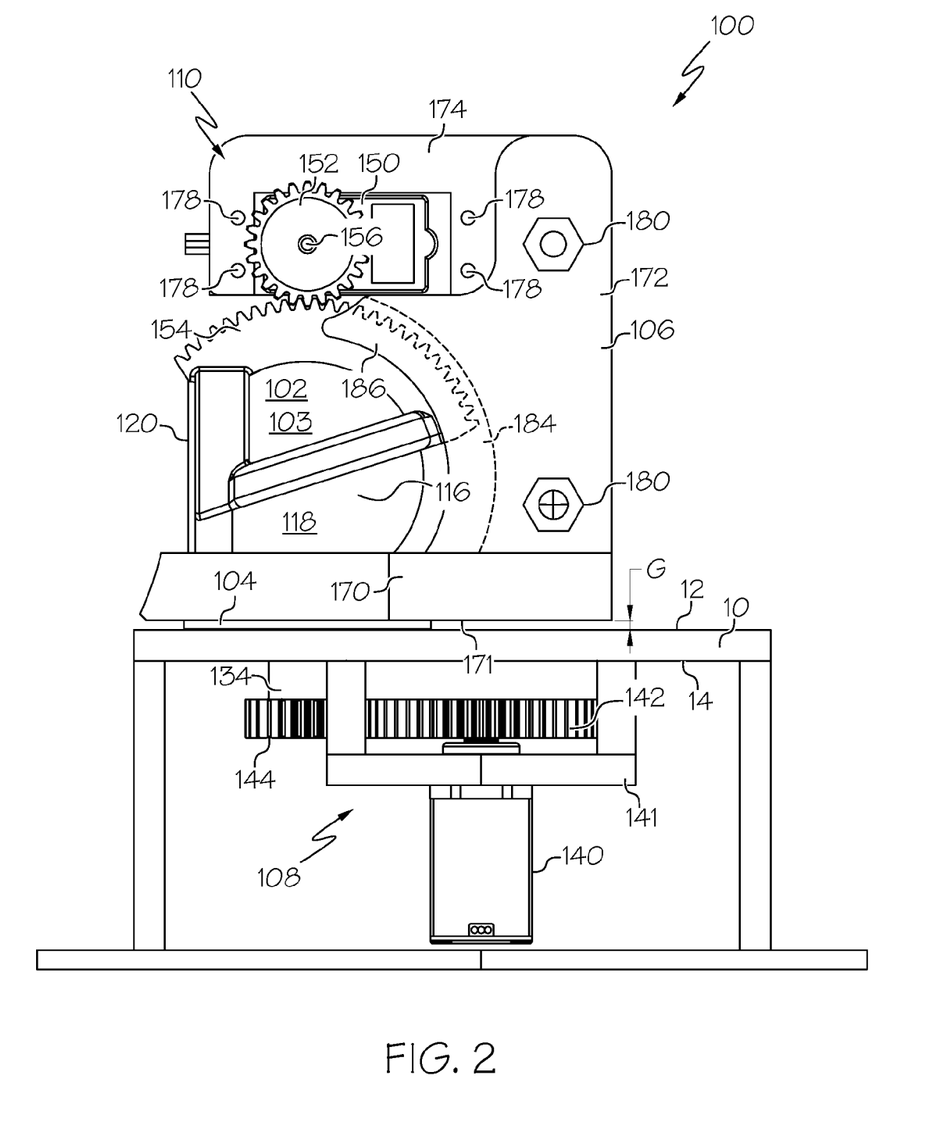
FIG. 2 is a side elevational view of the optical target orienting system of FIG. 1 (shown with the controller omitted)
Figure 3:
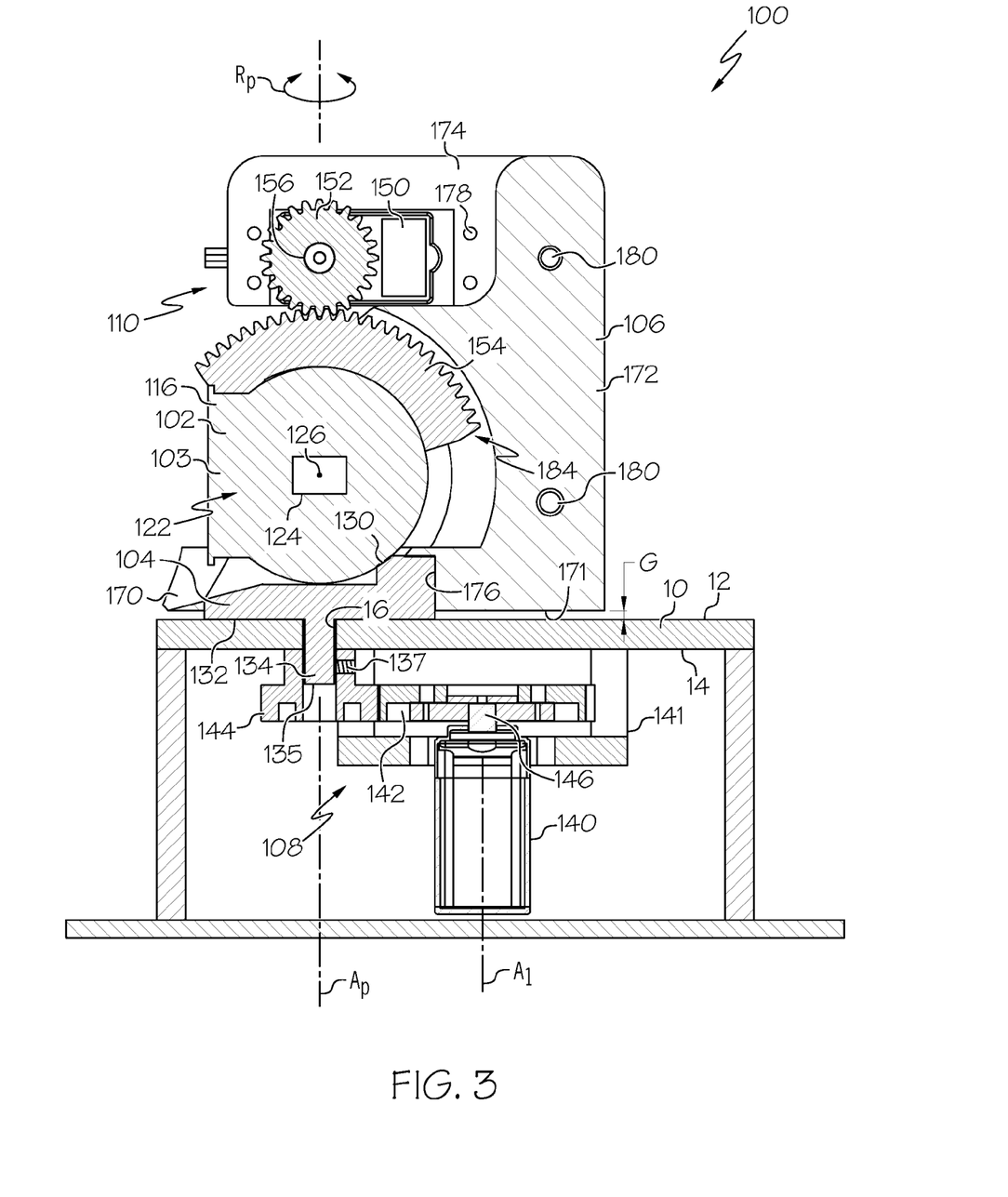
FIG. 3 is a side cross-sectional view of the optical target orienting system shown in FIG. 2.

Referring to FIGS. 1-3, one embodiment of the disclosed optical target orienting system, generally designated 100, may include an optical target 102, a mount 104, a support structure 106, a pan assembly 108, a tilt assembly 110 and a controller 112. The optical target orienting system 100 may be positioned on an object 10, such as a component (e.g., the airframe 418 (FIG. 7)) of an aircraft 402 (FIG. 7), to facilitate optically measuring (e.g., with light sources 202, 206 (FIG. 4)) the object 10.

The optical target 102 of the optical target orienting system 100 may be (or may include) a retroreflector. In one particular implementation, the optical target 102 may be a spherically mounted retroreflector 103. Spherically mounted retroreflectors 103 are well known in the art, and may include a spherical housing 116 having an outer surface 118 and defining an aperture 120 into the internal volume 122 (FIG. 3) of the spherical housing 116. A retroreflector 124, such as a corner cube mirror or the like, may be housed within the spherical housing 116 such that the vertex 126 of the retroreflector 124 is substantially centered within the spherical housing 116.

As best shown in FIG. 3, the mount 104 of the optical target orienting system 100 may define a nest 130 and an underside surface 132 vertically opposed from the nest 130. The nest 130 may be centered in the mount 104, and may be sized and shaped to receive therein a portion of the spherically mounted retroreflector 103. Optionally, the mount 104 may be (or may include) a magnet such that a magnetic connection may be made between the mount 104 and the spherically mounted retroreflector 103 when the spherically mounted retroreflector 103 is positioned in the nest 130 of the mount 104.

As shown in FIG. 1, the spherically mounted retroreflector 103 may be rotatable (arrow $R_T$) relative to the mount 104 about a tilt axis $A_T$. Such rotation (arrow $R_T$) about the tilt axis $A_T$ may be effected without the need for disengaging the spherically mounted retroreflector 103 from the nest 130 of the mount 104. Because the vertex 126 (FIG. 3) of the retroreflector 124 (FIG. 3) is substantially centered within the spherical housing 116 of the spherically mounted retroreflector 103, the position of the vertex 126 may remain substantially constant despite rotation (arrow $R_T$) of the spherically mounted retroreflector 103 relative to the mount 104 about the tilt axis $A_T$.

Referring back to FIG. 3, a shaft 134 may protrude from the underside surface 132 of the mount 104. The shaft 134 may be substantially centered relative to the mount 104, and may define a pan axis $A_P$, which may be substantially perpendicular to the tilt axis $A_T$. Rotation (arrow $R_P$) of the mount 104 about the pan axis $A_P$ may cause corresponding rotation (arrow $R_P$) of the spherically mounted retroreflector 103 about the pan axis $A_P$. Because the vertex 126 of the retroreflector 124 is substantially centered within the spherical housing 116 of the spherically mounted retroreflector 103, the position of the vertex 126 may remain substantially constant despite rotation (arrow $R_P$) of the mount 104 and the spherically mounted retroreflector 103 about the pan axis $A_P$.

As best shown in FIG. 3, the mount 104 may facilitate positioning the optical target orienting system 100 on the object 10. Specifically, the object 10 may have a first (e.g., mounting) surface 12 and a second (e.g., underside) surface 14, and may define an opening 16 that may extend from the first surface 12 to the second surface 14. The opening 16 may be sized and shaped to closely receive the shaft 134 of the mount 104. Therefore, the mount 104 may be positioned on the object 10 by inserting the shaft 134 of the mount 104 through the opening 16 in the object 10 such that the underside surface 132 of the mount 104 flushly abuts the first surface 12 of the object 10. When the mount 104 is properly positioned, the distal end 135 of the shaft 134 may protrude below the second surface 14 of the object 10.

With the mount 104 and the spherically mounted retroreflector 103 properly positioned on the object 10, the position of the vertex 126 relative to the object 10 may be known. Furthermore, the position of the vertex 126 relative to the object 10 may remain substantially constant, even as the mount 104 and the spherically mounted retroreflector 103 rotate (arrow $R_P$) about the pan axis $A_P$ and/or the spherically mounted retroreflector 103 rotates (arrow $R_T$) relative to the mount 104 about the tilt axis $A_T$.

Various commercially available spherically mounted retroreflectors and associated mounts may be used as the spherically mounted retroreflector 103 and the mount 104 of the disclosed optical target orienting system 100. The commercially available spherically mounted retroreflector and associated mount chosen for use as the spherically mounted retroreflector 103 and the mount 104 of the disclosed optical target orienting system 100 may be certified to ensure that the position of the vertex 126 may remain substantially constant, within a tight tolerance, despite rotation (arrow $R_P$) of the mount 104 and the spherically mounted retroreflector 103 about the pan axis $A_P$ and/or rotation (arrow $R_T$) of the spherically mounted retroreflector 103 relative to the mount 104 about the tilt axis $A_T$. Those skilled in the art will appreciate that using a certified spherically mounted retroreflector 103 and a certified mount 104 as described herein may eliminate the need for certifying the disclosed optical target orienting system 100.

The pan assembly 108 of the optical target orienting system 100 may be operatively connected to the mount 104 to effect rotation (arrow $R_P$) of the mount 104 and associated spherically mounted retroreflector 103 about the pan axis $A_P$. While a specific, servo motor and gear-based pan assembly 108 is shown and described, those skilled in the art will appreciate that various assemblies, whether electrically powered, hydraulically powered, pneumatically powered or otherwise powered, may be used to effect the desired rotation (arrow $R_P$) of the mount 104 and associated spherically mounted retroreflector 103 about the pan axis $A_P$.

As best shown in FIGS. 2 and 3, in one particular construction, the pan assembly 108 may include a pan actuator 140 and one or more coupling members 142, 144 that operatively connect the pan actuator 140 to the mount 104. The pan actuator 140 may be an electrical actuator, such as a first servo motor, and may have an actuator shaft 146 extending therefrom. The actuator shaft 146 of the pan actuator 140 may rotate about a shaft axis $A_1$. A mounting structure 141 may facilitate mounting the pan actuator 140 in the desired orientation relative to the mount 104.

The coupling members 142, 144 of the pan assembly 108 may translate the rotation of the actuator shaft 146 of the pan actuator 140 into rotation (arrow $R_P$) of the mount 104 (and associated spherically mounted retroreflector 103) about the pan axis $A_P$, as shown in FIG. 3. For example, the first coupling member 142 may be a gear mounted on the actuator shaft 146 of the pan actuator 140 and the second coupling member 144 may be a gear mounted on the distal end 135 of the shaft 134 of the mount 104. For example, a mechanical fastener 137, such as a set screw, may be used to connect the second coupling member 144 to the distal end 135 of the shaft 134.

The first gear (coupling member) 142 of the pan assembly 108 may be meshed with the second gear (coupling member) 144. Optionally, one or more intermediate gears (not shown) may be disposed between the first gear (coupling member) 142 and the second gear (coupling member) 144. Therefore, when the pan actuator 140 is actuated, rotation of the actuator shaft 146 of the pan actuator 140 causes rotation of the first gear (coupling member) 142, which causes rotation of the second gear (coupling member) 144, which causes rotation of the shaft 134 and, thus, rotation of the mount 104 and associated spherically mounted retroreflector 103.

Referring to FIG. 1, the controller 112 may be in communication with the pan actuator 140 of the pan assembly 108, as shown by communication line 148. The controller 112 may be a manual input device (e.g., a remote control) or a software-based device, such as a computer or other processing device. The controller 112 may be capable of controlling actuation of the pan actuator 140, including the direction of the actuation (e.g., clockwise versus counter-clockwise) and the magnitude of the actuation. Communication between the controller 112 and the pan actuator 140 may be wired (e.g., a physical cable) or wireless (e.g., infrared or radio frequency, such as Bluetooth®). Furthermore, communication between the controller 112 and the pan actuator 140 may be one-way, such as commands from the controller 112 to the pan actuator 140, or two-way, such as commands from the controller 112 to the pan actuator 140 and feedback (e.g., position/encoder data) from the pan actuator 140 to the controller 112.

The tilt assembly 110 of the optical target orienting system 100 may be operatively connected to the spherically mounted retroreflector 103 to effect rotation (arrow $R_T$) of the spherically mounted retroreflector 103 relative to the mount 104 about the tilt axis $A_T$. While a specific, servo motor and gear-based tilt assembly 110 is shown and described, those skilled in the art will appreciate that various assemblies, whether electrically powered, hydraulically powered, pneumatically powered or otherwise powered, may be used to effect the desired rotation (arrow $R_T$) of the spherically mounted retroreflector 103 relative to the mount 104 about the tilt axis $A_T$.

As shown in FIGS. 1-3, in one particular construction, the tilt assembly 110 may include a tilt actuator 150 and one or more coupling members 152, 154 that operatively connect the tilt actuator 150 to the spherically mounted retroreflector 103. The tilt actuator 150 may be an electrical actuator, such as a second servo motor, and may have an actuator shaft 156 extending therefrom. The actuator shaft 156 of the tilt actuator 150 may rotate about a shaft axis $A_2$ (FIG. 1).

The coupling members 152, 154 of the tilt assembly 110 may translate the rotation of the actuator shaft 156 of the tilt actuator 150 into rotation (arrow $R_T$) of the spherically mounted retroreflector 103 relative to the mount 104 about the tilt axis $A_T$, as shown in FIG. 1. For example, the first coupling member 152 may be a gear mounted on the actuator shaft 156 of the tilt actuator 150. The second coupling member 154 may be a gear mounted on or disposed around the outer surface 118 of the spherical housing 116 of the spherically mounted retroreflector 103. The first coupling member 152 may rotatably engage the second coupling member 154 such that rotation of the actuator shaft 156 rotates the second coupling member 154 and the optical target or spherically mounted retroreflector 103 relative to the mount 104. A mounting bracket 158 may be used to connect the second coupling member 154 to the outer surface 118 of the spherical housing 116 of the spherically mounted retroreflector 103.

The first gear (coupling member) 152 of the tilt assembly 110 may be meshed with the second gear (coupling member) 154. Optionally, one or more intermediate gears (not shown) may be disposed between the first gear (coupling member) 152 and the second gear (coupling member) 154. Therefore, when the tilt actuator 150 is actuated, rotation of the actuator shaft 156 of the tilt actuator 150 causes rotation of the first gear (coupling member) 152 about the shaft axis $A_2$ (FIG. 1), which causes rotation of the second gear (coupling member) 154, thereby rotating (arrow $R_T$) the spherically mounted retroreflector 103 relative to the mount 104 about the tilt axis $A_T$.

As shown in FIG. 1, the controller 112 may be in communication with the tilt actuator 150 of the tilt assembly 110, as shown by communication line 160, to control actuation of the tilt actuator 150, including the direction of the actuation (e.g., clockwise versus counter-clockwise) and the magnitude of the actuation. Communication between the controller 112 and the tilt actuator 150 may be wired (e.g., a physical cable) or wireless (e.g., infrared or radio frequency, such as Bluetooth®). Furthermore, communication between the controller 112 and the tilt actuator 150 may be one-way, such as commands from the controller 112 to the tilt actuator 150, or two-way, such as commands from the controller 112 to the tilt actuator 150 and feedback (e.g., position/encoder data) from the tilt actuator 150 to the controller 112.

The support structure 106 of the optical target orienting system 100 may position the tilt actuator 150 and the first coupling member 152 of the tilt assembly 110 relative to the second coupling member 154 (and associated spherically mounted retroreflector 103) to facilitate rotating (arrow $R_T$ in FIG. 1) the spherically mounted retroreflector 103 relative to the mount 104 about the tilt axis $A_T$ (FIG. 1). The support structure 106 may be connected to the mount 104 such that the tilt actuator 150 and the first coupling member 152 remain engaged with the second coupling member 154 while the mount 104 and the spherically mounted retroreflector 103 are rotating (arrow $R_P$ in FIG. 3) about the pan axis $A_P$.

The support structure 106 may include a base portion 170, a riser portion 172 and an extension portion 174. The base portion 170, the riser portion 172 and the extension portion 174 may be integral (formed as a single monolithic body) or, alternatively, one or more of the base portion 170, the riser portion 172 and the extension portion 174 may be formed separately and then connected together (e.g., by mechanical fasteners, welding, bonding or the like) to form the support structure 106. For example, as shown in FIGS. 1-3, the extension portion 174 may be one piece and the base portion 170 and the riser portion 172 may be another piece, and the extension portion 174 may be connected to the riser portion 172 with mechanical fasteners.

The support structure 106 may be formed from various materials or combinations of materials. Material selection may not be critical, but the material (or combination of materials) used should be sufficiently rigid to ensure proper functionality. Examples of suitable materials for forming the support structure 106 include, but are not limited to, metals, metal alloys, polymeric materials, composites (e.g., reinforced plastics) and cellulosic materials.

The base portion 170 of the support structure 106 may be fixedly connected to the mount 104 such that the support structure 106 moves with the mount 104 as the mount 104 (and associated spherically mounted retroreflector 103) rotates (arrow $R_P$) about the pan axis $A_P$. For example, as best shown in FIG. 3, the base portion 170 may define an opening 176 and the mount 104 may be at least partially received in the opening 176. The connection between base portion 170 and the mount 104 may be achieved by press-fitting the mount 104 into the opening 176. However, other techniques for fixedly connecting the mount 104 to the base portion 170 of the support structure 106, such as mechanical fasteners (e.g., one or more set screws), may be used without departing from the scope of the present disclosure.

The connection between the base portion 170 of the support structure 106 and the mount 104 may be such that the support structure 106 does not interfere with the abutting engagement between the underside surface 132 of the mount 104 and the first surface 12 of the object 10. For example, the support structure 106 may be design such that a gap G (FIGS. 2 and 3) is formed between the underside 171 of the base portion 170 and the first surface 12 of the object 10.

The extension portion 174 of the support structure 106 may support the tilt actuator 150 (and associated first coupling member 152) of the tilt assembly 110 such that the first coupling member 152 is engaged with the second coupling member 154. For example, the tilt actuator 150 may be connected to the extension portion 174 with mechanical fasteners 178 (e.g., nuts and bolts).

The riser portion 172 of the support structure 106 may elevate the extension portion 174 relative to the base portion 170. Specifically, the riser portion 172 may position the extension portion 174 vertically over the spherically mounted retroreflector 103 such that the first coupling member 152 (coupled to the tilt actuator 150) is engaged with the second coupling member 154.

The riser portion 172 of the support structure 106 may define a channel 184 (FIGS. 2 and 3). The channel 184 may be laterally bounded by wing portions 186 (FIGS. 1 and 2). As the tilt assembly 110 moves the second coupling member 154, thereby causing the spherically mounted retroreflector 103 to rotate (arrow $R_T$) about the tilt axis $A_T$, the second coupling member 154 (or at least a portion thereof) may move through the channel 184. As the second coupling member 154 moves through the channel 184, the wing portions 186 may inhibit movement/shifting of the second coupling member 154 out of the channel 184, thereby ensuring the second coupling member 154 remains engaged with the first coupling member 152.

Accordingly, the aperture 120 of the spherically mounted retroreflector 103 of the disclosed optical target orienting system 100 may be oriented about the pan axis $A_P$ (FIG. 3) and the tilt axis $A_T$ (FIG. 1) by selectively actuating the pan assembly 108 and the tilt assembly 110. When the disclosed optical target orienting system 100 employs a certified spherically mounted retroreflector 103 and a certified mount 104, the optical target orienting system 100 need not be separately certified because the pan assembly 108 and the tilt assembly 110 that effect movement of the spherically mounted retroreflector 103 and the mount 104 do not affect the certifications of the spherically mounted retroreflector 103 and the mount 104.

According to another aspect of the present disclosure, an optical target orientation system is described that is configured for use with an optical target, such as a spherical retroreflector, for orienting the spherical retroreflector 103. As shown in FIGS. 1-3, the optical target orienting system comprises a mount 104 defining a nest 130 and an underside surface 132 opposed from the nest 130, where the mount 104 includes a shaft 134 extending outward from the underside surface 132 and along a pan axis. The nest is configured to support a spherical retroreflector 103 positioned on the mount 104, in a manner such that the spherical retroreflector 103 is rotatable relative to the mount 104 about a tilt axis that is substantially perpendicular to the pan axis. The optical target orientation system further includes a first servo motor 140 operatively connected to the shaft 134 to rotate the mount 104 about the pan axis, and a second servo motor 150 positioned or arranged to rotate about the tilt axis and configured to engage a spherical retroreflector 103 positioned in the nest 130, to rotate the spherical retroreflector 130 relative to the mount 104 about the tilt axis. The optical target orienting system may further comprise a controller 112 configured to actuate the first servo motor 140 and the second servo motor 150. The controller 112 may include a wireless receiver component, and may be configured to transmit commands or signals to actuate the first servo motor (or pan actuator 140) and rotate the spherical retroreflector 103 about the pan axis in response to a first input signal received from a wireless remote control device 190 (shown in FIG. 4). The controller 112 maybe configured to transmit commands or signals to actuate the second servo motor (or tilt actuator 150) and rotate the spherical retroreflector 103 about the tilt axis in response to a second input signal received from a wireless remote control device 190. In this manner, the controller 112 enables remote control for adjustably rotating and orienting the spherical retroreflector 103 from a location remote from the optical target system. Accordingly, the optical target orienting system may comprises a controller 112 configured to actuate the first servo motor and the second servo motor in response to respective first and second input signals received from a remote control device 190, whereby the controller 112 enables control of the optical target orienting system for adjustably rotating and orienting the spherical retroreflector 103 from a location that is remote from the optical target system.

Figure 4:
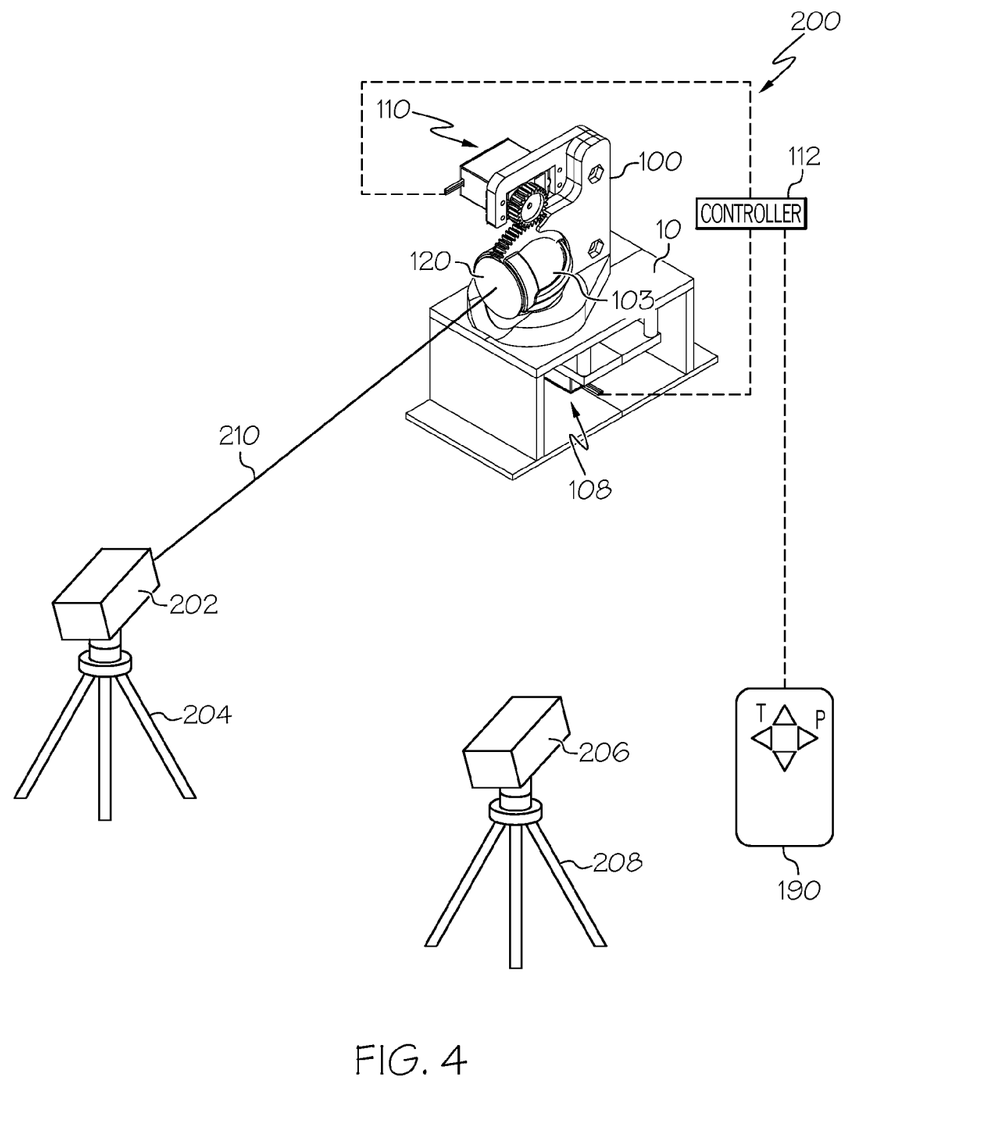
FIG. 4 depicts an example optical dimensional metrology system employing the disclosed optical target orienting system.

Referring to FIG. 4, an optical dimensional metrology system, generally designated 200, may include the disclosed optical target orienting system 100, a first light source 202 (e.g., a first laser tracker), which may be mounted on a first support 204 (e.g., a first tripod), and a second light source 206 (e.g., a second laser tracker), which may be mounted on a second support 208 (e.g., a second tripod). The optical target orienting system 100 may be positioned on an object 10. The aperture 120 of the spherically mounted retroreflector 103 of the optical target orienting system 100 may be aligned with the first light source 202 (e.g., the angle of the beam 210 projected by the first light source 202 relative to the aperture 120 may be within the angle of acceptance of the laser tracker 202).

Thus, at least a portion of the beam 210 projected from the first light source 202 to the optical target orienting system 100 may be reflected back to the first light source 202, thereby facilitating the taking of an optical measurement. However, when a second optical measurement is to be taken at the same location on the object 10, but with the second light source 206, the aperture 120 of the spherically mounted retroreflector 103 of the optical target orienting system 100 must be moved into alignment with the second light source 206. Therefore, the controller 112 may send one or more actuation signals commanding the pan assembly 108 and/or the tilt assembly 110 to move the aperture 120 of the spherically mounted retroreflector 103 into alignment with the second light source 206.

Figure 5:
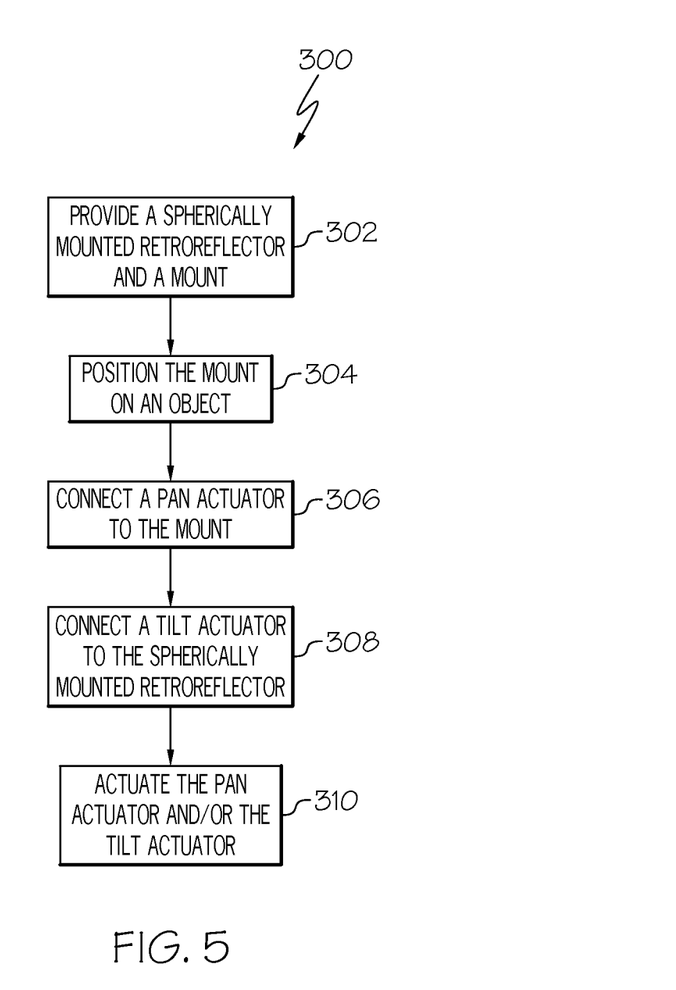
FIG. 5 is a flow diagram depicting one embodiment of the disclosed optical target orienting method.

Referring to FIG. 5, one embodiment of the disclosed method for optical target alignment, generally designated 300, may begin at Block 302 with the step of providing an optical target 102 and mount 104 for the optical target 102. The optical target 102 may be a spherically mounted retroreflector 103 and the mount 104 may be specially designed to support the spherically mounted retroreflector 103. Both the spherically mounted retroreflector 103 and the mount 104 may be certified, as is known and common in the art.

At Block 304, the mount 104 may be positioned on an object 10. The object 10 may have a surface 12 and may define an opening 16. The mount 104 may be positioned on the object 10 such that the shaft 134 of the mount 104 extends through the opening 16 in the object 10 and the underside surface 132 of the mount 104 flushly abuts the surface 12 of the object 10.

At Block 306, a pan actuator 140 may be operatively connected to the mount 104 such that upon actuation of the pan actuator 140, the mount 104 rotates (arrow $R_P$) about a pan axis $A_P$. For example, coupling members 142, 144, such as gears, may transfer energy from the pan actuator 140 to the mount 104 to effect the desired rotation (arrow $R_P$) of the mount 104 about the pan axis $A_P$.

At Block 308, a tilt actuator 150 may be operatively connected to the spherically mounted retroreflector 103 such that upon actuation of the tilt actuator 150, the spherically mounted retroreflector 103 rotates (arrow $R_T$) relative to the mount 104 about a tilt axis $A_T$. For example, coupling members 152, 154, such as gears, may transfer energy from the tilt actuator 150 to the spherically mounted retroreflector 103 to effect the desired rotation (arrow $R_T$) of the spherically mounted retroreflector 103 about the tilt axis $A_T$.

At Block 310, the pan actuator 140, the tilt actuator 150 or both the pan actuator 140 and the tilt actuator 150 may be actuated to effect desired rotation of the spherically mounted retroreflector 103 about the pan axis $A_P$, the tilt axis $A_T$ or both the pan axis $A_P$ and the tilt axis $A_T$. The actuation may be controlled such that the aperture 120 of the spherically mounted retroreflector 103 assumes the desired orientation. For example, the actuation may be controlled such that the aperture 120 of the spherically mounted retroreflector 103 is aligned with a light source 202, such as a laser tracker.

Figure 6:
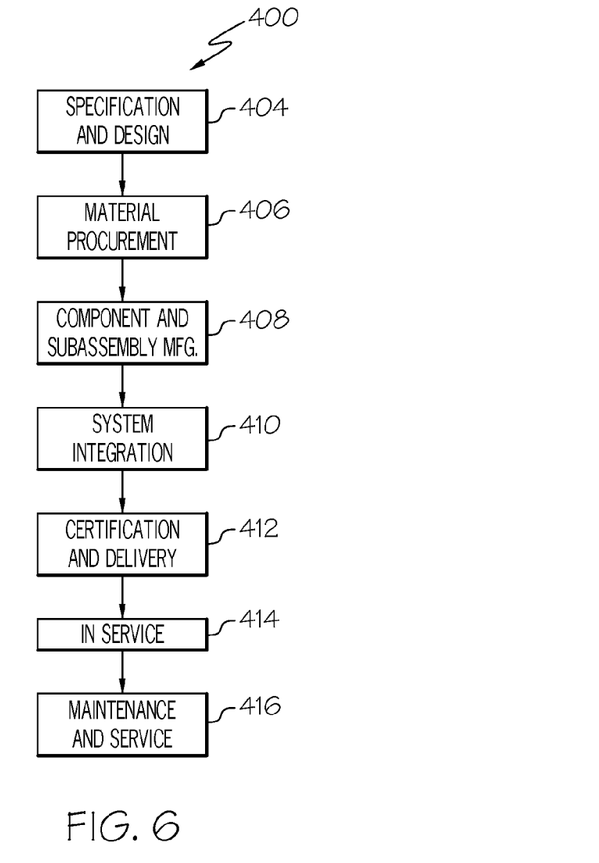
FIG. 6 is flow diagram of an aircraft manufacturing and service methodology.
Figure 7:
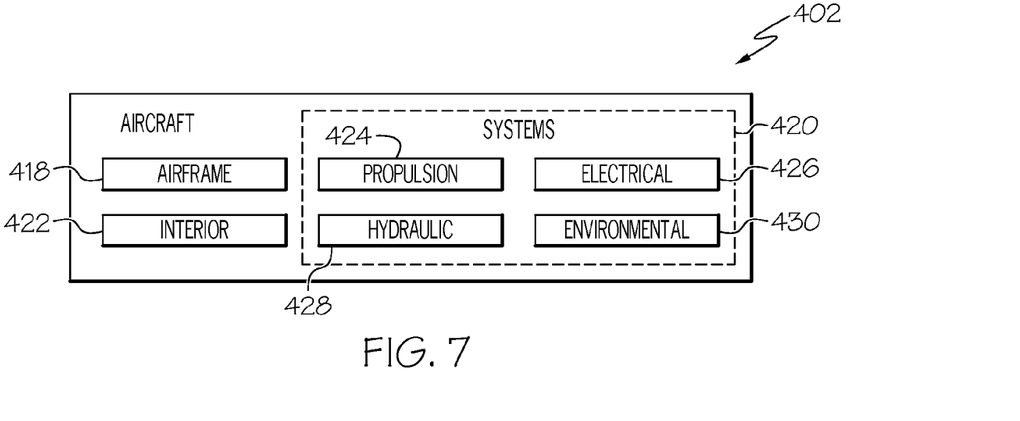
FIG. 7 is a block diagram of an aircraft.

Examples of the disclosure may be described in the context of an aircraft manufacturing and service method 400, as shown in FIG. 6, and an aircraft 402, as shown in FIG. 7. During pre-production, the aircraft manufacturing and service method 400 may include specification and design 404 of the aircraft 402 and material procurement 406. During production, component/subassembly manufacturing 408 and system integration 410 of the aircraft 402 takes place. Thereafter, the aircraft 402 may go through certification and delivery 412 in order to be placed in service 414. While in service by a customer, the aircraft 402 is scheduled for routine maintenance and service 416, which may also include modification, reconfiguration, refurbishment and the like.

Each of the processes of method 400 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 7, the aircraft 402 produced by example method 400 may include an airframe 418 with a plurality of systems 420 and an interior 422. Examples of the plurality of systems 420 may include one or more of a propulsion system 424, an electrical system 426, a hydraulic system 428, and an environmental system 430. Any number of other systems may be included.

The disclosed optical target orienting system and method may be employed during any one or more of the stages of the aircraft manufacturing and service method 400. As one example, the disclosed optical target orienting system and method may be employed during material procurement 406. As another example, components or subassemblies corresponding to component/subassembly manufacturing 408, system integration 410, and or maintenance and service 416 may be fabricated or manufactured using the disclosed optical target orienting system and method. As another example, the airframe 418 and/or the interior 422 may be constructed using the disclosed optical target orienting system and method. Also, one or more apparatus examples, method examples, or a combination thereof may be utilized during component/subassembly manufacturing 408 and/or system integration 410, for example, by substantially expediting assembly of or reducing the cost of an aircraft 402, such as the airframe 418 and/or the interior 422. Similarly, one or more of system examples, method examples, or a combination thereof may be utilized while the aircraft 402 is in service, for example and without limitation, to maintenance and service 416.

The disclosed optical target orienting system and method are described in the context of an aircraft; however, one of ordinary skill in the art will readily recognize that the disclosed optical target orienting system and method may be utilized for a variety of vehicles, as well as for non-vehicle applications. For example, implementations of the embodiments described herein may be implemented in any type of vehicle including, e.g., helicopters, passenger ships, automobiles and the like.

Although various embodiments of the disclosed optical target orienting system and method have been shown and described, modifications may occur to those skilled in the art upon reading the specification. The present application includes such modifications and is limited only by the scope of the claims.

What is claimed is:

1. An optical target orienting system comprising:
   a mount defining a nest and a pan axis;
   a spherically mounted retroreflector positioned in said nest, said spherically mounted retroreflector comprising an aperture and being rotatable relative to said mount about a tilt axis;
   a pan assembly operatively connected to said mount to rotate said mount and, thus, said spherically mounted retroreflector about said pan axis;
   a tilt assembly operatively connected to said spherically mounted retroreflector to rotate said spherically mounted retroreflector relative to said mount about said tilt axis; and
   a support structure comprising:
      a base portion defining an opening, wherein said mount is received in said opening;
      an extension portion supporting said tilt assembly; and
      a riser portion extending from said base portion to said extension portion.

2. The optical target orienting system of claim 1 wherein said spherically mounted retroreflector is magnetically connected to said mount.

3. The optical target orienting system of claim 1 wherein said tilt axis is substantially perpendicular to said pan axis.

4. The optical target orienting system of claim 1 wherein said mount comprises a shaft extending therefrom, said shaft being axially aligned with said pan axis.

5. The optical target orienting system of claim 4 wherein said pan assembly comprises a pan actuator operatively connected to said shaft.

6. The optical target orienting system of claim 5 wherein said pan actuator comprises a servo motor.

7. The optical target orienting system of claim 5 further comprising a controller in communication with said pan actuator.

8. The optical target orienting system of claim 5 wherein said pan assembly further comprises a first coupling member connected to an actuator shaft of said pan actuator and a second coupling member connected to said shaft of said mount.

9. The optical target orienting system of claim 1 wherein said tilt assembly comprises a tilt actuator operatively connected to said spherically mounted retroreflector.

10. The optical target orienting system of claim 9 wherein said tilt actuator comprises a servo motor.

11. The optical target orienting system of claim 9 further comprising a controller in communication with said tilt actuator.

12. The optical target orienting system of claim 9 wherein said tilt assembly further comprises a first coupling member connected to an actuator shaft of said tilt actuator and a second coupling member connected to said spherically mounted retroreflector.

13. The optical target orienting system of claim 12 wherein said riser portion defines a channel, and wherein at least a portion of said second coupling member extends into said channel.

14. An optical target orienting system comprising:
   a mount defining a nest and an underside surface opposed from said nest, said mount comprising a shaft extending outward from said underside surface and along a pan axis;
   the nest being configured to support a spherical retroreflector positioned thereon in a manner such that the spherical retroreflector is rotatable relative to said mount about a tilt axis, wherein said tilt axis is substantially perpendicular to said pan axis;
   a first servo motor operatively connected to said shaft to rotate said mount about said pan axis;
   a second servo motor arranged to rotate about the tilt axis and configured to engage a spherical retroreflector positioned on the nest, to rotate said retroreflector relative to said mount about said tilt axis; and
   a support structure comprising:
      a base portion defining an opening, wherein said mount is received in said opening;
      an extension portion supporting said second servo motor; and
      a riser portion extending from said base portion to said extension portion.

15. The optical target orienting system of claim 14 further comprising a controller configured to actuate the first servo motor and the second servo motor in response to respective first and second input signals received from a remote control device, whereby the controller enables control of the optical target from a location remote from the optical target system.

16. A method for orienting an aperture of a spherically mounted retroreflector, said spherically mounted retroreflector being positioned in a nest defined by a mount, said method comprising:
   positioning said mount on an object such that an underside surface of said mount flushly abuts said object;
   operatively connecting a pan actuator to said mount such that actuation of said pan actuator causes said mount to rotate about a pan axis;
   operatively connecting a tilt actuator to said spherically mounted retroreflector such that actuation of said tilt actuator causes said spherically mounted retroreflector to rotate within said nest relative to said mount about a tilt axis; and
   actuating at least one of said pan actuator and said tilt actuator to move said aperture of said spherically mounted retroreflector into alignment with a light source.

17. The method of claim 16 wherein said tilt axis is substantially perpendicular to said pan axis.

18. The optical target orienting system of claim 1 wherein said mount comprises a first underside surface and said base portion comprises a second underside surface, and wherein said first underside surface is vertically displaced from said second underside surface to define a gap between said second underside surface and an object when said mount is positioned on said object.

19. An optical dimension metrology system comprising said optical target orienting system of claim 1, and further comprising:
   a first light source aligned with said aperture of said spherically mounted retroreflector; and
   a second light source out of alignment with said aperture of said spherically mounted retroreflector, wherein actuation of at least one of said pan assembly and said tilt assembly causes said aperture of said spherically mounted retroreflector to move into alignment with said second light source.

20. The optical target orienting system of claim 14 wherein said base portion comprises an underside surface, and wherein said underside surface of said mount is vertically displaced from said underside surface of said base portion to define a gap between said underside surface of said base portion and an object when said mount is positioned on said object.

21. The method of claim 16 wherein said light source is a laser tracker of an optical dimension metrology system.

* * * * *